(12) United States Patent
Shachar et al.

(10) Patent No.: US 11,567,068 B2
(45) Date of Patent: Jan. 31, 2023

(54) DETECTION OF CARDIAC TROPONIN OR BIOLOGICAL MARKERS VIA SHEAR HORIZONTAL SURFACE ACOUSTIC WAVE BIOSENSOR USING A WET-DRY BIOANALYTICAL TECHNIQUE

(71) Applicant: Sensor Kinesis Corp., Los Angeles, CA (US)

(72) Inventors: Yehoshua Shachar, Santa Monica, CA (US); Marlon S. Thomas, Riverside, CA (US)

(73) Assignee: Autonomous Medical Devices Inc., Santa Ana, CA (US)

( * ) Notice: Subject to any disclaimer, the term of this patent is extended or adjusted under 35 U.S.C. 154(b) by 446 days.

(21) Appl. No.: 16/368,583

(22) Filed: Mar. 28, 2019

(65) Prior Publication Data
US 2020/0309737 A1    Oct. 1, 2020

(51) Int. Cl.
| | |
|---|---|
| *G01N 33/543* | (2006.01) |
| *G01N 29/02* | (2006.01) |
| *G01N 33/536* | (2006.01) |
| *A61B 5/318* | (2021.01) |

(52) U.S. Cl.
CPC ....... *G01N 33/54373* (2013.01); *A61B 5/318* (2021.01); *G01N 29/022* (2013.01); *G01N 33/536* (2013.01); *G01N 2291/0255* (2013.01); *G01N 2291/02809* (2013.01)

(58) Field of Classification Search
CPC .............. G01N 33/536; G01N 33/543; G01N 29/022; G01N 2291/0255; G01N 2291/02809
See application file for complete search history.

(56) References Cited

U.S. PATENT DOCUMENTS

| | | | | |
|---|---|---|---|---|
| 2011/0053139 A1* | 3/2011 | Larson | ................. | G01N 33/553 435/5 |
| 2011/0256640 A1* | 10/2011 | Dittmer | ............ | G01N 33/54373 436/501 |
| 2012/0329142 A1* | 12/2012 | Battrell | ................. | C12Q 1/686 435/287.2 |
| 2016/0091497 A1* | 3/2016 | Goix | .................. | G01N 33/6893 506/9 |

\* cited by examiner

*Primary Examiner* — Gailene Gabel (74) *Attorney, Agent, or Firm* — Marcus C. Dawes; Daniel L. Dawes (57) ABSTRACT

The illustrated embodiments include a method of operating a SAW sensor to detect a sample in a fluid which includes the steps of: providing a SAW sensor with a functionalized detection lane in a handheld, portable assay device and sensor system; maintaining the functionalized detection lane of the SAW sensor dry until the sample is fluidically disposed in the detection lane; fluidically disposing the sample in the functionalized detection lane; removing fluid the functionalized detection lane to concentrate the sample in the functionalized detection lane to increase the probability of a specific antibody-antigen interaction; washing the functionalized detection lane so that substantially only the specific antigen-antibody interaction remains in the functionalized detection lane; removing fluid from the functionalized detection lane again; and measuring concentration of the sample while the functionalized detection lane is fluid-free.

21 Claims, 4 Drawing Sheets

Table 1. SH-SAW Sensor Sensitivity to Changes in Solution Viscosity

| Glycerol Solution | Delta Phase |
|---|---|
| 0.002% | 3.37714 |
| 0.02% | 3.98297 |
| 0.2% | 4.6983 |
| 2.0% | 18.738639 |
| 20% | 87.7541739 |

| [cTn] | Phase Shif | STDev |
|---|---|---|
| 24000 | 92.27 | 29.28 |
| 2400 | 57.32 | 26.47 |
| 240 | 29.85 | 8.88 |
| 24 | 5.753 | |
| 2.4 | 1.68 | 1.05 |
| 0.24 | 2.88 | 2.88 |
| 0.012 | 1.77 | |

DETECTION OF CARDIAC TROPONIN OR BIOLOGICAL MARKERS VIA SHEAR HORIZONTAL SURFACE ACOUSTIC WAVE BIOSENSOR USING A WET-DRY BIOANALYTICAL TECHNIQUE

BACKGROUND

Field of the Technology

The invention relates to the field of diagnostic microanalysis of biological agents, factors or markers using a surface acoustic wave (SAW) sensor. In particular, the invention relates to an apparatus and method for using a shear horizontal (SH) surface acoustic wave (SAW) biosensor to detect the binding of target antigens to specific antibodies that are immobilized on a piezo-electric substrate (lithium tantalite) via immunochemical reaction.

Description of the Prior Art

A model system has been developed to examine the receptor-ligand interaction between the tripeptide, cardiac troponin (troponin I-T-C complex) or troponin sub-unit I and antibodies to recognize epitopes on the troponin I sub-unit. The troponin is a tripeptide complex (subunits C, T, and I) located on thin filaments of the skeletal and cardiac muscle fibers. Troponin C is the calcium-binding component, troponin T is the tropomyosin-binding component, and troponin I is the inhibitory component. Since the isoforms of troponin C are identical in the skeletal muscle and cardiac muscle, troponin C concentration in blood is not specific for myocardial injury. The isoforms of troponin T and troponin I differ from the skeletal and the cardiac muscle, and thus are specific for cardiac tissue necrosis. Troponin T is present chiefly in the bound form to the contractile elements of the myocardial cells; however, it is also present free in the cytoplasm. Troponin T exhibits a dual release initially of the cytoplasmic component and later of the bound component. Troponin sub-unit I has a single isoform and is extremely specific for the cardiac muscle and has not been isolated from the skeletal muscle.

This absolute specificity makes it an ideal marker of myocardial injury. They are released into the circulation 6-8 h after myocardial injury, peak at 12-24 h and remain elevated for 7-10 days (42). The only disadvantage of cTn is the late clearance, which precludes diagnosis of a recurrent myocardial infarction. To address this issue, multiple troponin measurements are taken sequentially to determine if levels are rising, falling, or remaining constant.

Notwithstanding, troponin I and troponin T has become the globally recognized standard biomarkers for the diagnosis of acute myocardial infarction (AMI). Recent technological advancements in immunosensing and secondary amplification techniques have pushed detection limits well below 1 ng/mL, resulting in development of high-sensitivity cardiac troponin (hs-cTn) assays. While these are now being implemented worldwide, such assays are limited in portability, expensive to run and maintain, and require experienced technical training to use. Thus, there remains an urgent need for a portable hs-cTn assay and sensor system that is facile and expedient.

BRIEF SUMMARY

The illustrated embodiments include a method of operating a SAW sensor to detect a sample in a fluid which includes the steps of: providing a SAW sensor with a functionalized detection lane in a handheld, portable assay and sensor system; maintaining the functionalized detection lane of the SAW sensor dry until the sample is fluidicly disposed in the detection lane; fluidicly disposing the sample in the functionalized detection lane; removing fluid the functionalized detection lane to concentrate the sample in the functionalized detection lane to increase the probability of a specific antibody-antigen interaction; washing the functionalized detection lane so that substantially only the specific antigen-antibody interaction remains in the functionalized detection lane; removing fluid from the functionalized detection lane again; and measuring concentration of the sample while the functionalized detection lane is fluid-free.

The method includes: taking a second sample at a later time; repeating the steps of maintaining the functionalized detection lane of the SAW sensor dry until the second sample is fluidicly disposed in the detection lane, fluidicly disposing the second sample in the functionalized detection lane, removing fluid the functionalized detection lane to concentrate the second sample in the functionalized detection lane to increase the probability of a specific antibody-antigen interaction, washing the functionalized detection lane so that substantially only the specific antigen-antibody interaction remains in the functionalized detection lane, removing fluid from the functionalized detection lane again; and measuring concentration of the second sample while the functionalized detection lane is fluid-free a second later time to establish whether the sample concentration is increasing or decreasing in time.

The sample includes cardiac troponin and further includes the steps of providing a SAW sensor with a functionalized detection lane in a facile portable assay and sensor system which is operable without experienced technical training.

The step of measuring concentration of the sample while the functionalized detection lane is fluid-free includes the step of measuring the concentration of the sample while the functionalized detection lane is fluid-free at concentration levels at or below 10 pg/ml.

The method further includes the step of performing an additional test for myocardial infarction at or about the same time.

The step of performing the additional test includes the step of performing a multiplexed measurement of multiple biomarkers.

The sample is cardiac troponin and further includes the step of performing an additional test for myocardial infarction at or about the same time.

The step of performing the additional test includes the step of performing an electrocardiogram (EKG).

The step of performing the multiplexed measurement of multiple biomarkers includes the step of performing both troponin C and I measurements for an equimolar test, or performing tests for creatine kinase (CK) and/or myoglobin (MB). to increase confidence of testing for cTnI results.

The step of measuring the concentration of the sample while the functionalized detection lane is fluid-free includes the step of simultaneously measuring concentrations of analytes in the sample in multiple functionalized detection lanes of the SAW senor, while the functionalized detection lane is fluid-free.

The step of simultaneously measuring concentrations of analytes in the sample in multiple functionalized detection lanes of the SAW senor, while the functionalized detection lane is fluid-free includes the step of simultaneously measuring concentrations of the analytes in the sample in multiple functionalized detection lanes of the SAW senor, while each of the functionalized detection lane is fluid-free.

The step of measuring concentration of the sample while the functionalized detection lane is fluid-free comprises measuring concentration of the sample while the functionalized detection lane is fluid-free in a calibrated dynamic range of 2 pg/ml to 24 µg/ml of analyte.

The step of measuring concentration of the sample while the functionalized detection lane is fluid-free in a calibrated dynamic range of 2 pg/ml to 24 µg/ml of analyte comprises measuring concentration of the sample while the functionalized detection lane is fluid-free in a calibrated dynamic range of 2 pg/ml to 24 µg/ml of troponin I.

The step of providing a SAW sensor with functionalized detection lane in a handheld, portable assay and sensor system includes the steps of providing a SAW sensor in a sensor spin-disk system utilizing a spinning disk cartridge in which rotationally generated forces separate erythrocytes, leukocytes and platelets from a whole blood sample, where the spinning disk cartridge includes chambers for the introduction of nanoparticle conjugates to a sensing region of the SAW sensor, for mixing and for washing of the sample, and for moving the sample around the cartridge, where the SAW sensor is integrated into the spinning disk cartridge thereby removing the need to move the sample to another device or chamber for measurement, thereby resulting in reduction of analysis time so that an assay of the sample is available in 10 minutes or less after disposing the whole blood sample into the system.

The method further includes the steps of taking multiple samples at about the same time; repeating maintaining the functionalized detection lane of the SAW sensor dry until the second sample is fluidicly disposed in the detection lane, fluidicly disposing the second sample in the functionalized detection lane, removing fluid the functionalized detection lane to concentrate the second sample in the functionalized detection lane to increase the probability of a specific antibody-antigen interaction, washing the functionalized detection lane so that substantially only the specific antigen-antibody interaction remains in the functionalized detection lane, removing fluid from the functionalized detection lane again until sufficient mass of the sample has been disposed in the functionalized detection lane to produce a reliable reading; and then measuring concentration of the sample while the functionalized detection lane is fluid-free.

The illustrated embodiments can also be characterized as a wet-dry method including the steps of: disposing a pre-determined limited volume of a liquid sample including an analyte through a sensing area of a SAW detector, which sensing area has been functionalized with a predetermined antibody; disposing a predetermined limited volume of a liquid sample including an analyte through a reference area of a SAW detector, which reference area has not been functionalized with the predetermined antibody; maintaining the liquid sample in contact with the sensing area of the SAW detector for a time period longer than the time required for the analyte to diffuse from liquid to the predetermined antibody and find the proper orientation for binding to the antibody in order to likely be immobilized on the sensing area; evaporating the liquid sample from the sensing area and reference area; and generating a differential measurement signal from the sensing area and reference area indicative of the amount of analyte bound to the sensing area after evaporation.

The method further includes the steps of repeating disposing a predetermined limited volume of an additional liquid sample including an analyte through a sensing area of a SAW detector, disposing a predetermined limited volume of the additional liquid sample including an analyte through the reference area of a SAW detector, maintaining the additional liquid sample in contact with the sensing area of the SAW detector for a time period longer than the time required for the analyte to diffuse from liquid to the predetermined antibody and find the proper orientation for binding to the antibody in order to likely be immobilized on the sensing area, and evaporating the additional liquid sample from the sensing area and reference area to increase the probability that the analyte will make a pairing with the antibody in the proper orientation, leading to specific capture in the sensing area prior to measurement.

The method further includes the step of disposing a gasket over the sensing area to restrictively define the portion of the sensing area to which the liquid sample binds.

The spirit and scope of the illustrated embodiments also include an apparatus for performing the above methods.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1:
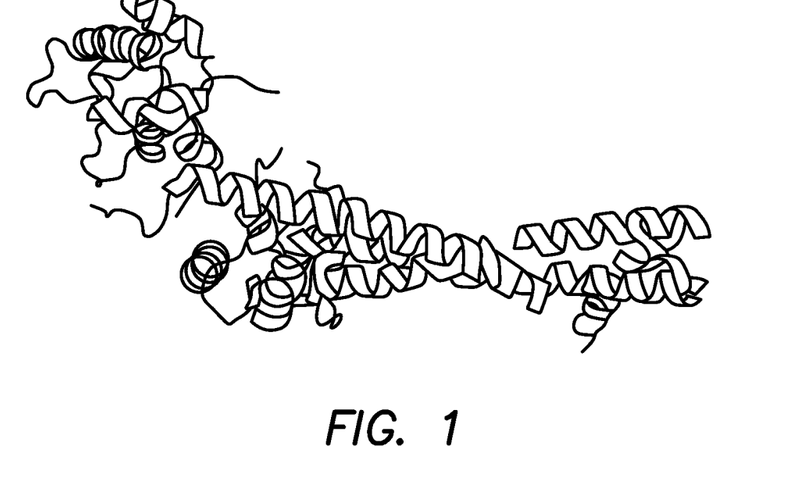
FIG. 1 is a diagrammatic ribbon representation of the human cardiac troponin complex (52 kDa core) in the calcium-saturated form. Blue=troponin C; green=troponin I; magenta=troponin T.

Cardiac troponin I (cTnI) measurements have become an indispensable tool for risk stratification and outcomes assessment in patients who are suspected of having acute coronary syndrome (ACS). A ribbon diagram of cardiac troponin is shown in FIG. 1. A highly portable sensor capable of monitoring a patient's blood for troponin represents a significant advancement towards providing bedside measurements to any patient, anywhere on the globe.

cTnI is indicative of the disease state or it may even function as an early indicator of disease on-set. Because circulating cTnI complex or sub-unit I are naturally at lower concentrations than 10 pg/ml in human blood, the sensor platform needs to be capable of detecting concentrations below 10 pg/mL. There are several commonly occurring conditions that can increase troponin concentrations without increasing the patient's risk of an acute myocardial infarction (AMI). For this reason, clinicians need to be aware of the possible non-cardiac reasons for increases in troponin I concentrations. To minimize the possibility of misdiagnosis or false positive assessments, troponin assessment is typically performed with other determinations. For example, a doctor would typically order a work-up including both an EKG and a blood testing for cTn I to assist in the differential diagnosis. It is estimated that greater 95% of all circulating cTnI occurs as cTnI-cTnC complex. Therefore, one potential method for increasing the confidence of the cTnI results would be to provide a multiplexed measurement of multiple biomarkers; for instance, including both troponin C and I measurements for an equimolar test, or including tests for creatine kinase (CK) and/or myoglobin (MB).

Figure 6:
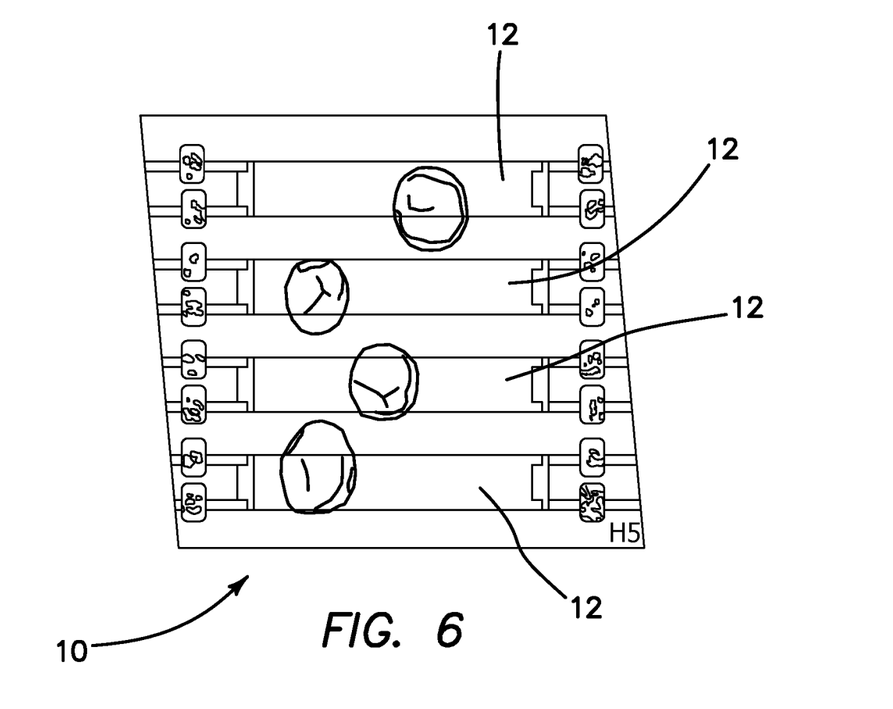
FIG. 6 is a photograph of a multi-channel SH-SAW sensor, shown in isolation of any circuit into which it is included and into which samples have been pipetted.

With multiple detection lanes 12 in a single SAW sensor 10 as shown in FIG. 6, a shear wave surface acoustic wave (SH-SAW) sensor 10 is well-suited to perform multiplexed assays. The need for measuring multiple biomarkers for a proper diagnosis is certainly not limited to acute myocardial infarction (AMI). Indeed, several disease models, including multiple forms of cancer, viral infections, and fungal pathogens, require tests for multiple biomarkers for diagnosis and treatment. All of these biochemical assays can be detected by immunoassays that can be performed in an SH-SAW bioassay.

Figure 8:
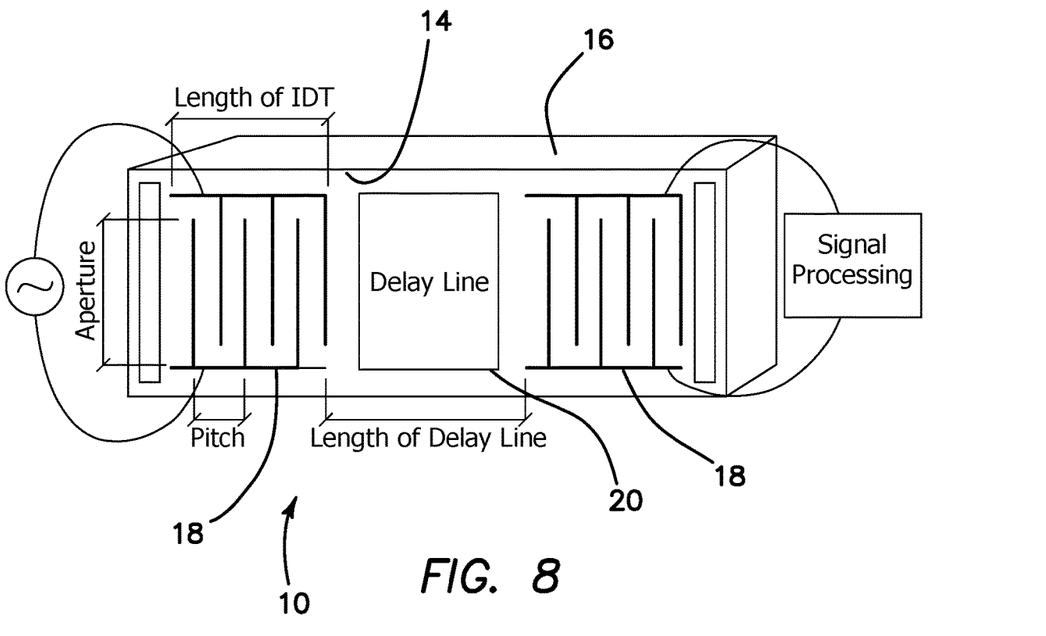
FIG. 8 is a schematic diagram of the SH-SAW sensor comprising a composite thin film of silicon dioxide deposited on a lithium tantalite substrate featuring a pair of interdigital electrodes (IDTs).

The SAW sensor 10 is comprised of a composite thin film 14 of silicon dioxide deposited on a lithium tantalite substrate 16 featuring a pair of interdigital electrodes (IDTs) 18 as diagrammatically depicted in FIG. 8 and as described in U.S. Pat. No. 8,709,791, incorporated herein by reference as if set out in its entirety. The silicon dioxide layer 14 serves two purposes: 1) to provide a scaffold for biofunctionalization with capturing agents (usually antibodies or DNA probes); and 2) to serve as a waveguide 20 to confine the SH-SAW wave to the waveguide 20 and a superficial layer about one wavelength on the top surface of the SAW sensor 10. Therefore, the SAW sensor 10 only probes the solid-liquid interface and not the bulk solution. Naturally, the assumption is made that the concentration of the analyte at the surface is representative of the bulk solution. For detection of troponin, the top surface of the silicon dioxide waveguide 20 is functionalized by immobilizing antibodies that are targeted against binding epitopes on the human cardiac troponin, subunit I.

Beneath the top layer 14 of $SiO_2$ on opposite ends of the SAW sensor 10 are the IDTs 18. In our device, the IDT structure 18 is precisely tuned to transduce a signal in the range of 325 or 650 MHz. The IDTs 18 are designed in such a way as to excite the lithium tantalite (LiTaO3) crystal of substrate 16, and in the process, generate a pressure wave (acoustic wave). Prior to the fabrication of the SH-SAW sensor 10, the $LiTaO_3$ crystal of substrate 16 was cut to a 36° Y-cut with X-axis propagation shape to promote the propagation of shear waves in the crystal. The propagation of shear waves in the SH-SAW sensor 10 is described as a leaky surface acoustic wave propagation, because some of the energy from the wave is lost due to the viscosity of the solvent. The $LiTaO_3$ crystal with cut to a 36° Y-cut with X-axis propagation is capable of liquid handling due to the silicon dioxide guiding layer, however, the system is most sensitive in air since there is little attenuation of the acoustic wave due either solvent viscosity or due to mass loading from a liquid solvent. Air offers very little viscosity or mass loading, therefore, the sensitivity of the SH-SAW sensor 10 in air is significantly higher than the sensitivity in a liquid environment.

When one IDT array 18 is excited by an RF input waveform of appropriate frequency, the signal is transmitted through the $LiTaO_3$ substrate 16 in the form of an SH-SAW wave and received by the IDT array 18 on the opposite end. The rate of propagation and attenuation of this wave are highly sensitive to the material properties of the region separating the two IDTs 18; this is the sensing area or delay line of waveguide 20. Changes to the sensing area 20 that alter the transmission of the SH-SAW wave include alterations in the viscoelastic properties including rendering the viscoelastic layer rigid due to binding of the antigen to the antibody, due to increases or decreases in temperature, and due to addition or removal of mass at the solid-liquid interface. Thus, the addition of mass to the surface associated with the binding and formation of antibody-antigen complexes is the basis of sensing for the SAW system 10. The method by which the alteration of SH-SAW wave is transformed into a diagnostic measurement is discussed further below.

Diagnostics Background:

The ability to accurately obtain concentrations of small molecules and protein biomarkers is a critical requirement for monitoring disease progression and for early diagnostics. However, this is complicated because the levels of biomarkers in circulating blood is often at trace levels. For this reason, the detection of biomarkers typically requires either a concentration step or the sensor utilized must be very sensitive. Traditional methods of performing biomarker detection involves performing an immunodiagnostic biochemical assay. Immunodiagnostic assays for the protein antigens take many forms and can be perform using several class of sensing modalities. These modalities include enzyme-linked immunoassays, fluorescence immunoassays, electrophoretic immunoassays, electrochemical impedance immunoassays and mass spectroscopy immunoassays. Each of these systems have its own disadvantages. These techniques all have the disadvantages of requiring a labeled marker, long processing times, and require large bulky equipment. Thus, there has been a demand for hand-held point-of-care devices that have the sensitivity of these instruments. Immunoassays performed using protein-coated chips in hand-held biosensors has a tremendous potential to revolutionize medicine.

In these hand-held point-of-care systems, antigen detection is performed using surface bound antibodies that serve as the recognition elements. One an antibody, successfully pairs with an antigen, it induces a change in a signal which is transmitted electrically. The assay sensitivity therefore dependent on the number of antigens that are immobilized. In the case of the SH-SAW sensor 10, the binding of the antigens to the surface bound antibodies impacts the propagation on the acoustic wave. The factors that influence the capture efficiency include the surface density, the antibody orientation on the surface, and the solvent used. The covalent attachment of the antibodies is performed using an epoxy-terminated trimethoxy silane linker. In an ideal scenario, we want to immobilize the antibodies in their native forms. Here we present a user friendly and rapid SAW sensor 10 for monitoring human blood for biomarkers.

SH-SAW Waves Background:

The phenomenon of surface waves was first described by Lord Rayleigh from 1877. However, the first reports of a chemical sensor that was based on SAW technology was a vapor sensor that appeared in an issue of Analytical Chemistry from August 1979. Since this early report, the SAW devices have been attractive for use as gas sensors. However, longitudinal and shear vertical components of the Rayleigh waves are significantly attenuated in liquids, which limited their use as chemical sensors. To overcome this limitation, Love wave devices were developed and optimized. This class of piezo-electric devices uses a guiding layer over the substrate to protect the sensor from harsh liquids environments, serve as an acoustic waveguide to prevent direct interaction between the liquid and the acoustic wave, and confine the energy of the surface wave to the solid-liquid interface. The displacement of a particle on the surface of waveguide 20 of the SAW sensor 10 attenuates both the velocity and amplitude of the surface acoustic wave that is generated by the excitation of the piezo-electric substrate 16. The SH-SAW devices use a guiding layer, an acoustic waveguide 20, to confine a surface acoustic wave in a region within one wave length to the surface of the SAW sensor 10. The main requirement is that the waveguide have a lower wave velocity than the substrate 16 used to fabricate the SAW sensor 10. Without the waveguide, the bare SH-SAW device 10 has a lower sensitivity because the acoustic wave goes deeper into the substrate 16. In the case of lithium tantalate, the SH wave velocity is ~4077 m/s for the 36-degree Y-cut with X-propagation. The guiding layer used on the SH-SAW devices is silicon dioxide layer 14.

The performance of the SH-SAW sensor 10 at the working frequency can be determined automatically by scanning over a small range or frequencies (±1 MHz) around the center frequency that the SAW chip was designed to operate. This allows one to finely tune the excitation frequency such that the SAW sensor 10 performs at the highest gain possible. Despite this of these efforts, some energy is always lost due a combination of several factors including sample viscosity or mass of sample present in the medium. Maximizing the signal-to-noise ratio, therefore, becomes an effort of minimizing the insertion losses, maximizing the specific signal due to mass loading on the sensor surface, increasing viscosity on the sensor surface, and increasing rigidity due to binding on the surface.

The samples are introduced to the reader (not shown) via a sample chamber (not shown) or well using a pipette, syringe or a syringe pump. The tested sample is traditionally introduced into a liquid sample containing a set volume of buffer solution to cover the entire surface area of waveguide 20 of the SAW sensor 10. Here we propose an alternative method of reducing the volume of the liquid introduced to a single droplet of sample or a series of droplets as shown in FIG. 6. Alternatively, we could use a small volume between 0.5-5 µl. The antigens in the sample can interact with the sensory surface of waveguide 20 and reach a dynamic equilibrium. The liquid from the sample is completely evaporated. After evaporation, we follow up with a wash step and then allow the sample to dry a second time. The new endpoint is then compared to the endpoint of a reference lane 24 by subtracting the signal measured from reference lane 24 from the sample or detection lane 12. The difference between the endpoint from the sample lane 12 and the reference lanes 24 is the differential measurement that is used to calibrate the SAW sensor 10. We establish a dynamic range between 2 picogram per milliliter (2 pg/ml) and 24 micrograms per milliliter (24 µg/ml). This range spans the clinically relevant range of 10 pg/ml-100 ng/ml. This allows the SH-SAW sensor 10 to assess normal concentration of troponin I, slightly elevated troponin levels and high troponin levels from a single measurement. A second measurement performed one hour later establishes if the value is on the leading or trailing edge, i.e. has an increasing or decreasing slope.

In a first embodiment, evaporation is a natural evaporation process which takes place at the temperature, pressure and humidity of the environment in which sensor 10 is disposed. This environment can vary in humidity and other parameters depending on place and time. Although in general heating of sensor 10 to dry it is not desired because of the presence of biologically active molecules, it is possible that heating will not denature proteins, nucleic acids or carbohydrates below 100° F., however, it may alter the natural biological activity. In another embodiment drying by flowing a stream of dry gas over the droplet or sample may be employed to enhance or reduce the time of analysis. For example, flowing a stream of dry nitrogen through sensor 10 is one embodiment, since nitrogen is a relatively inert gas that should not alter any biological activity.

In yet another embodiment sequentially drying is used, namely dry-resuspend or add more liquid—and then dry again. This has two advantages: Increase the overall mass of the analyte; and it allows multiple attempts for proper antibody-antigen conjugation. Besides (a) having a short diffusion length (due to the small droplet or sample size), concentration of the sample to due to evaporation and maximization of capture because the sample is distributed over only the sensing area. However, the ability to do sequential addition increases the odds for capture and increases the total deposited sample mass.

It is within the scope and spirit of the illustrated embodiments that a three dimensional sensing surface area could be provided in sensor 10 to increase the total sensing surface area. An increase in surface area would increase overall antigen capture on the sensor 10.

In one embodiment a moisture sensor (not shown) is provided so that the measurement process is only started or performed when a predetermined moisture level, e.g. 20% relative humidity, in a confined chamber after drying with a bone-dry gas is achieved. The sensing and reference lanes experience the same identical environmental conditions. The reference lane, however, does not have the ability to bind the antigen specifically. Only non-specific binding. The dryness of the sensing area can be monitored or programmed to be the same each time. The SH-SAW sensor 10 itself gives an indication of when the measured film is dry enough. There is a massive jump in the signal from sensor 10, when the required dryness is achieved. In a process where the liquid has not been removed to a critical or desired level, there is no dramatic shift in the sensitivity of the sensor 10. This shift always come at the end of the process when the measured film dries.

The handheld device (not shown) is a fully integrated system that takes whole blood and processes the blood into blood plasma and solids to facilitate a measurement. The handheld device and its method of operation is completely described in U.S. application Ser. No. 16/285,092, filed on Feb. 25, 2019, incorporated herein by reference in its entirety. Blood processing and cleanup of a fresh blood sample is performed in a disk-like cartridge (not shown) that spins at 2000 revolutions per minute (RPM) to separate erythrocytes, leukocytes and platelets from the liquid components of blood. The cartridge is designed with chambers (not shown) in the cartridge allows for the introduction of the nanoparticle conjugates to the sensing region of the SH-SAW sensors, mixing and washing of the assay. In addition to solving the issue of separating blood into its components, the disk also solves the issue of moving the liquid around the cartridge. The SH-SAW sensor 10 is integrated into the spinning disk removing the need to move the liquid sample to another device or another chamber. This results in reductions analysis times. This allows the disclosed system to give a result for a patient's sample in less than 30 minutes after presentation of the patient or 10 minutes after receiving a whole blood sample. The results from the SH-SAW analysis coefficients show variations of less than 10%. ANOVA analysis of variance reveals that the data collected from samples with a concentration range that span six orders of magnitude, revealed that each SH-SAW result fell within a 95% confidence limit with less than a 5% chance that the mean value was from another population for sample having concentrations between 2.4 ng/ml-24 µg/ml. The data points below 2.4 ng/ml required sequential addition of samples to increase the mass to get a signal. These values are also consistent and distinct, knowing that the mean value for each group was distinct with less a 5% chance that the values below to another statistical population.

SH-SAW Biochemical Assay

The goal of developing this SH-SAW biosensor platform is to enable the detection of biochemical interactions, specifically between the epitopes on a protein biomarker of interest and an antibody that is directed against these specific epitopes of that antigen. Typically, this is performed by adding a sample of approximately 50 µL of the sample solution to a well with some buffer solution already on the SAW sensor 10. This results in approximately a two-thirds dilution of the sample. This dilution can be beneficial in the case of a viscous sample or samples with complex matrices. However, due to challenges in sample handling and an effort to reduce the limits of detection, dilution of the sample is counter-productive.

Figure 7:
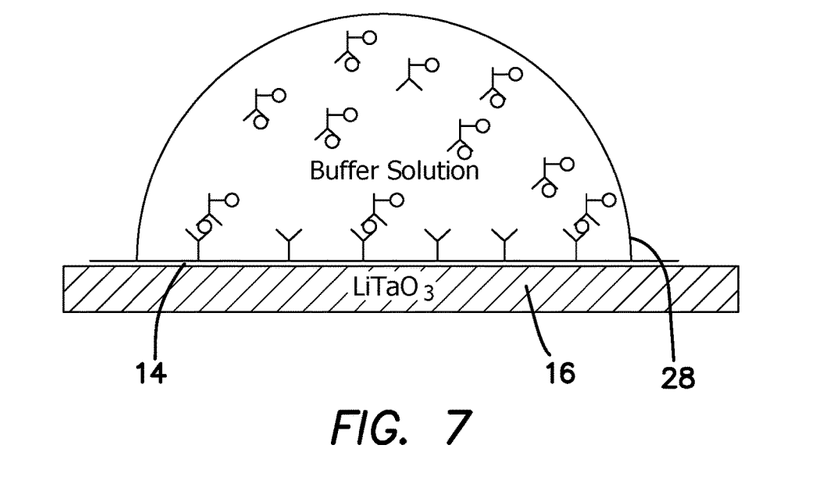
FIG. 7 is a schematic diagram of the wet-dry process of the illustrated embodiments.

To address this issue, we developed an alternative approach to performing SH-SAW measurements using a wet-dry method where the sensor remains dry until addition of the sample to the sensing surface of waveguide 20. This technique effectively eliminates the initial dilution and allows the sample to become highly concentrated on the sensing surface of waveguide 20 as the liquid evaporates. There are several distinct advantages of performing the wet-dry method over the previous "wet-wet" method: 1) elimination of the attenuation of acoustic wave due to the column of liquid over the detection lane 12; 2) reduction of the measurement to a pure mass measurement, which allows a simple wash step to ensure only the specific antigen-antibody interaction that we are interested in is being probed; and 3) the evaporation process serves as a concentration mechanism to increase the probability of specific antibody-antigen pairing. Taken together, these advantages will dramatically improve the signal-to-noise ratio.

In the wet-dry approach, a small volume of liquid sample, typically 50 µl, is pipetted or a continuous stream of liquid is flowed past a single delay line of waveguide 20. If the liquid remains in contact with the sensing area of waveguide 20 for a period that is longer than the time required for the molecule to diffuse from solution to the antibody and find the proper orientation for binding, then there is a high probability of the antibody being immobilized on the detection lane 12. In one iteration of the SH-SAW sensor 10, a gasket (not shown) is placed over the delay line of waveguide 20 to restrictively direct the area where the sample binds. The liquid samples evaporate as a function of time, humidity and the concentration of the molecules of the analyte in solution. If the rate of evaporation is high, the probability for proper antibody-antigen interaction increases significantly. Multiple administrations of a sample containing the antigen increases the probability that the antigen will make a pairing with the antibody in the proper orientation, leading to specific capture. The remaining lanes serve as reference lanes 24. The measured signal is calculated by comparing the endpoint after evaporation from the sample lane 12 and subtracting the signal of a sample in the reference lane 24. The sample in reference lane 24 contains a buffer solution void of all antigens. The samples will have an unknown concentration of cTnI. The wet-dry measurements are compatible with different types of mass enhancers including gold nanoparticles (AuNPs) and magnetic nanoparticles (MNPs).

In a biochemical assay, the SH-SAW sensor 10 is submerged and the mass of the biological layers that are formed by adsorption or selective binding of species from the bulk solution interacts with the acoustic wave propagation on the surface of the shear horizontal surface acoustic wave (SH-SAW) sensor 10. The phase shift induced by the retardation of the acoustic wave relative to the unperturbed wave, gives the phase shift. Eliminating the phase shift and signal attenuation induced by the column of liquid media dramatically increases the effects that viscous-elastic coupling has on the phase velocity. A simple model of the biosensor surface can be developed using a three-layer system consisting of a solid elastic substrate (LiTaO$_3$) 16, a viscoelastic middle layer 14 (silicon dioxide), and a viscoelastic top layer 26 (biological layer). In the solid substrate 16, the displacement field of the SH-SAW wave is given by the transverse wave equation, equation 1 below.

$$\text{The transverse wave equation } v_i = \sqrt{\frac{\mu_i}{\rho_i}} \quad \text{Equation 1}$$

Where $v_0$ is the speed of sound in the substrate (LiTaO$_3$), $\mu_0$ is the substrate elastic shear modulus and $\rho_i$ mass density of the substrate 16.

The propagation loss per wavelength is given by equation 2 below.

Equation 2. Propagational losses per wavelength $$\Delta PL = \frac{I_{Liq} - I_{Air}}{L}$$

Where $I_{Liq}$ is the device insertion loss when the flow cell is filled with liquid and $I_{Air}$ is the device insertion loss with an empty flow cell. The subtraction of these two terms does not account for Fresnel reflection at the solid-liquid interface.

Experimentally, it has been observed that the device propagation losses increase with the product of the square root of viscosity and density. The propagation loss per wavelength can therefore be represented as equation 3 below:

Equation 3. The propagational losses per wavelength $$\Delta PL = \frac{40\pi}{\text{Ln}10} S \sqrt{\frac{\omega \gamma \rho}{2}}$$

The phase velocity shift of a long-wavelength SH-SAW can be given as equation 4 below:

$$\frac{\Delta v}{v_0} = \frac{\Delta \varphi}{\varphi_0} \qquad \text{Equation 4}$$

Where $\Delta\varphi$ is the phase shift measured using a network analyzer and $\varphi_0$ is the unperturbed phase between input and output interdigitated transducers (IDTs) 18.

In the case of SH-SAW sensor 10 under viscous liquid loading, the relative phase velocity shift was found to be proportional to the square root of the liquid viscosity and given by the equation 5:

$$\text{The phase velocity shift} \frac{\Delta v}{v_0} - S\sqrt{\frac{\omega \gamma \rho}{2}}. \qquad \text{Equation 5}$$

If we do a plot of $$\frac{\Delta v}{v_0}$$

against $\sqrt{\gamma\rho}$ you get a linear relation in agreement with the theoretical model. The linear regression line in the plot has a slight negative offset from the origin. The extra relative velocity shift from the origin is due to the liquid loading. Removing the liquid eliminates these effects results in a positive offset.

Compared to the wet-wet technique, the wet-dry technique shows a higher sensitivity for mass sensing. This may be due to the fact that under the same processing conditions, the wet-dry technique results in thinner entrained viscous liquid. This leads to less perturbation of the propagating acoustic wave, i.e., a much lower insertion loss since the column of fluid above the delay line of waveguide 20 will be close to the maximum decay depth.

The SAW Chips

The multi-channel SH-SAW sensors 10, as described above, were fabricated on $LiTaO_3$ substrate 16 using lift-off photo-lithographic-lithographic methods. The fabrication process involves uses a $LiTaO_3$ substrate 16 in the following manner: 1) deposition of a series of metals to form an alloy, namely a sequence of deposition 200 Å titanium followed by 200 Å aluminum, followed by 500 Å silicon nitrile and then 0.75 µm silicon dioxide; 2) coating the top of the device with 50 Å titanium and then 1000 Å aluminum; 3) disposing a final layer is 100 Å of silicon dioxide. After the photo-lithographic methods were completed, the partially processed chip of the SAW sensor 10 were coated with an adhesion layer. The adhesion layer is a layer of epoxy-terminated tri-ethoxy silane. The epoxy-terminated tri-ethoxy silane is reactive with several functional groups. The epoxy group is highly reactive with free amine groups from polypeptides and various proteins and reacts through a ring-opening process. The chips of SAW sensor 10 are then cleaned and stored in an inert atmosphere free of moisture.

When chips of SAW sensor 10 are ready use, they are covalently decorated with targeting molecules such as IgGs and ScFvs. The free epoxy groups are quenched using a protein stabilization agent called Stabil Coat Immunoassay stabilizer (SurModics of Eden Prairie, Minn.). The functionalized chips of SH-SAW sensor 10 are stored in a dedicated chamber until used. The data from the readers can be further processed off-line using a spread sheet or data analysis tool Matlab.

Data Analysis

Data analysis is performed using a custom-designed graphical user interface (GUI) that was designed in an Agilent Vee Pro environment for data collection. Data processing is performed by a MatLab/SimuLink program that determines the phase delay, attenuation and normalizes the data to a known reference. The equation used in the computer to determine the change in phase and the conformational changes in the sample are:

$$\Delta P = \left\{ \frac{Slope_R}{Slope_S} \right\} \qquad \text{Equation 1}$$

$$\left\{ \frac{(Endpt_S - \text{Starting } pt_S) - ((Endpt_R - \text{Starting } pt_R)}{1} \right\} \left\{ \frac{ACR}{SCR} \right\}.$$

Where ACR is the average calibration curve response and SCR is the specific calibration curve response, and where the subscript R signifies a reference data point and subscript S signifies a sample data point. Equation 2 gives:

$$\frac{\Delta P}{\Delta A} = \left\{ \frac{\Delta P(Endpoint_S - \text{Starting } point_S) -}{(\Delta P(Endpoint_R - \text{Starting } point_R))}{Amp(Endpoint_S - \text{Starting } point_S) -}{(Amp(Endpoint_R - \text{Starting } point_R))} \right\} \left\{ \frac{ACR}{SCR} \right\}. \qquad \text{Equation 2}$$

Preliminary Data

Glycerol Calibration

Binary glycerol-water solutions behave essentially as Newtonian fluids, at concentration lower than 50% glycerol. The main difference between water and the glycerol-water mixture is the magnitude of the viscosity. Therefore, we can probe the effects of changing solution viscosity on the phase shift of the propagating acoustic wave being measured by the device.

Figure 2:
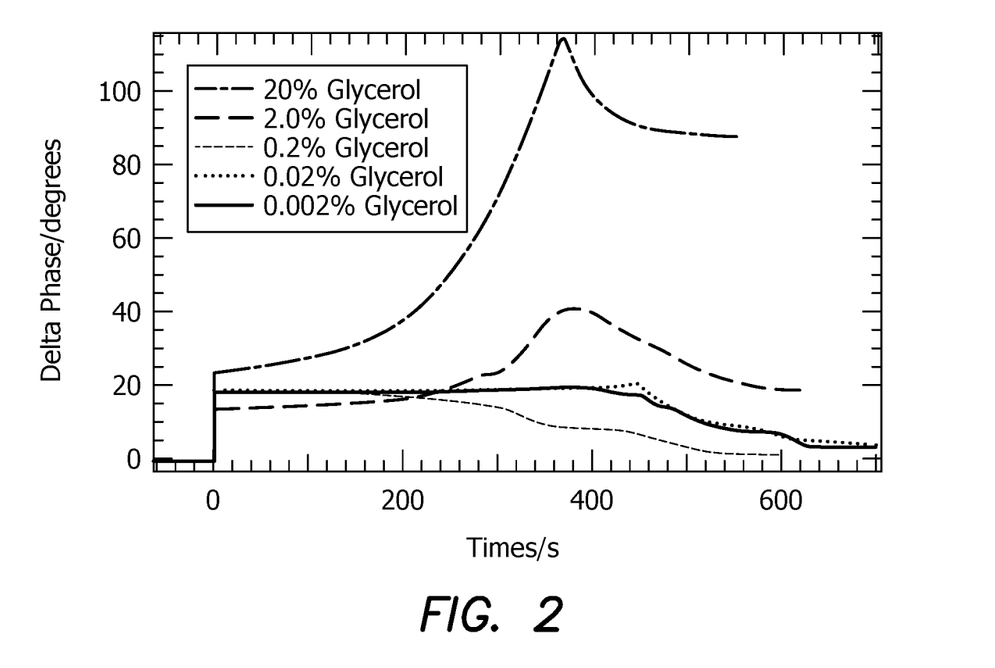
FIG. 2 is a graph of SAW phase shift output verses time to show the sensitivity of the SH-SAW detector to changing concentrations of glycerol.
Figure 3:
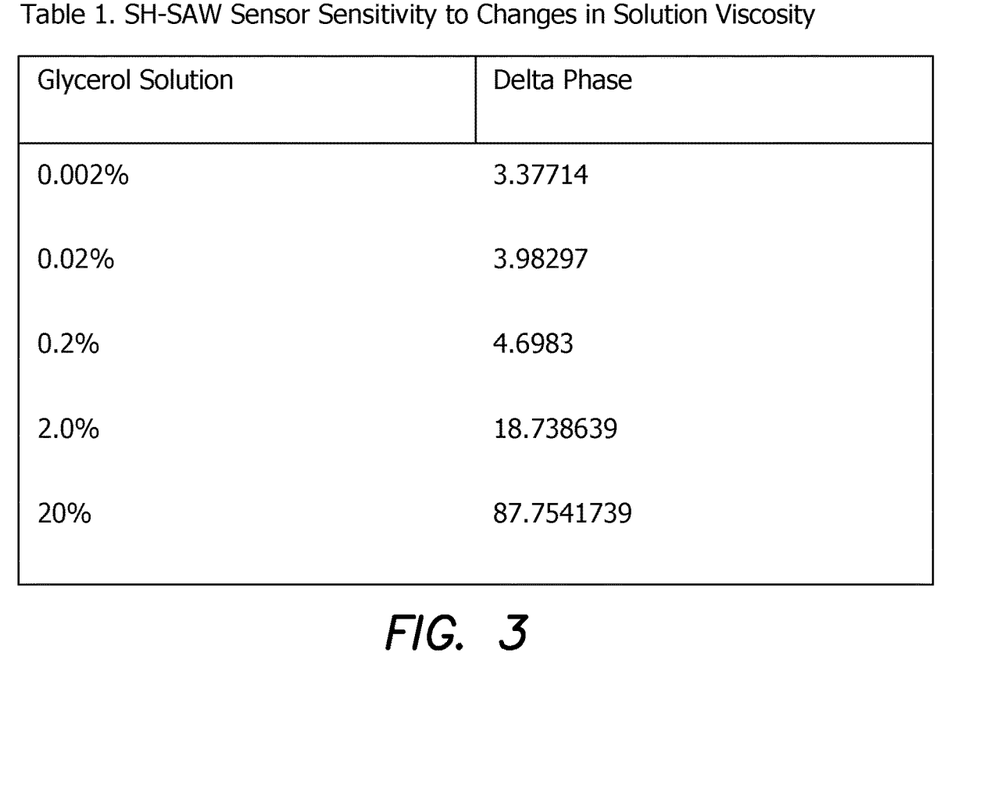
FIG. 3 is a table illustrating SH-SAW sensor sensitivity to changes in solution viscosity.
Figure 4:
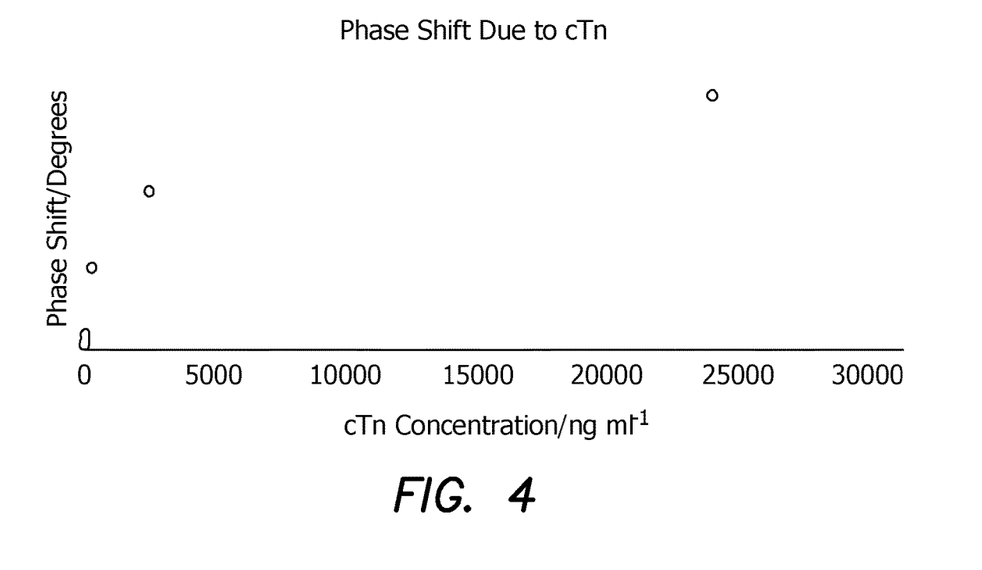
FIG. 4 is a graph of SAW phase shift due to CTn as a function of concentration illustrating the sensitivity of the SAW sensor as a function of troponin binding.
Figure 5:
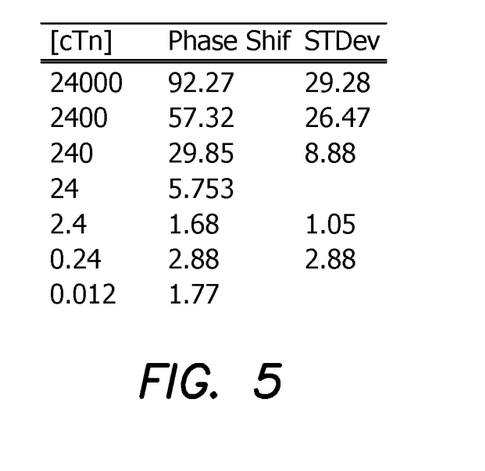
FIG. 5 is a table illustrating SH-SAW sensor sensitivity to cTn concentrations in a sodium phosphate buffer solution.

The calibration of the wet-dry method was performed using a binary solution of glycerol in deionized water that range from 0.002% glycerol to 20% glycerol. The temperature of the sensor was assumed to be approximately the sample for all measurements. However, the temperature was recorded for all experiments so the phase shift can be normalized for the effects of temperature of the acoustic wave propagation. Table 1 in FIG. 3 and the graph of FIG. 2 summaries the results from the glycerol-water study.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. A method of operating a SAW sensor to detect an analyte suspended in a first fluid sample taken from a patient, the method comprising:
providing a surface acoustic wave (SAW) sensor with at least one functionalized detection lane in a handheld, portable assay device and sensor system, the at least one functionalized detection lane consisting of a composite thin film coated with an antibody and disposed over a substrate;
fluidically disposing the fluid sample in the at least one functionalized detection lane;
concentrating the analyte at a surface of the at least one functionalized detection lane to concentrate the first sample and increase the probability of forming a complex comprising an analyte and an antibody bound to the at least one functionalized detection lane;
confining a signal from the SAW sensor to an interface between the first fluid sample and the composite thin film; and
measuring a concentration of the analyte originally suspended in the first fluid sample within the formed complex at the interface between the first fluid sample and the composite thin film of the at least one functionalized detection lane.

2. The method of claim 1 further comprising:
taking a second fluid sample from the patient at a later time;
repeating fluidically disposing the second fluid sample in the at least one functionalized detection lane, concentrating the analyte suspended in the second fluid sample at the surface of the at least one functionalized detection lane to concentrate the second sample and increase the probability of forming a specific analyte-antibody complex bound to the at least one functionalized detection lane;
measuring a concentration of the analyte originally suspended within the second fluid sample that is now within the formed complex at the interface between the second fluid sample and the composite thin film of the at least one functionalized detection lane; and
establishing whether the analyte concentration is increasing or decreasing in time by comparing the measured concentration of the analyte originally suspended in the first fluid sample bound only to the at least one functionalized detection lane with the measured concentration of the analyte originally suspended in the second fluid sample bound only to the at least one functionalized detection lane.

3. The method of claim 2 where the analyte within the second fluid sample comprises cardiac troponin.

4. The method of claim 1 where the analyte comprises cardiac troponin.

5. The method of claim 1 where measuring the concentration of the analyte originally suspended in the first fluid sample within the formed complex at the interface between the first fluid sample and the composite thin film of the at least one functionalized detection lane comprises measuring the concentration of the analyte originally suspended in the first fluid sample within the formed complex at the interface between the first fluid sample and the composite thin film of the at least one functionalized detection lane at concentration levels at or below 10 pg/mL.

6. The method of claim 1 further comprising performing test for myocardial infarction at or about the same time as measuring the concentration of the analyte originally suspended in the first fluid sample within the formed complex at the interface between the first fluid sample and the composite thin film of the at least one functionalized detection lane.

7. The method of claim 6 where performing the test for myocardial infarction comprises performing a multiplexed measurement of a plurality of biomarkers.

8. The method of claim 6 where performing the test for myocardial infarction comprises performing an electrocardiogram (EKG) at or about the same time as measuring the concentration of the analyte originally suspended in the first fluid sample within the formed complex at the interface between the first fluid sample and the composite thin film of the at least one functionalized detection lane.

9. The method of claim 1 where the analyte comprises cardiac troponin and where the method further comprises performing test for myocardial infarction at or about the sametime as measuring the concentration of the analyte originally suspended in the first fluid sample within the formed complex at the interface between the first fluid sample and the composite thin film of the at least one functionalized detection lane.

10. The method of claim 9 where performing the test for myocardial infarction comprises performing a multiplexed measurement of a plurality of biomarkers.

11. The method of claim 10 where performing the multiplexed measurement of the plurality of biomarkers comprises performing both troponin C and I measurements for an equimolar test, or performing tests for creatine kinase (CK) and/or myoglobin (MB) to increase confidence of testing for cTnI results.

12. The method of claim 1 where measuring the concentration of the analyte within the formed complex at the interface between the first fluid sample and the composite thin film of the at least one functionalized detection lane comprises simultaneously measuring concentrations of analytes in the first fluid sample within at least one formed complex at the interface between the first fluid sample and the composite thin film of a plurality of functionalized detection lanes of the SAW sensor.

13. The method of claim 12 where simultaneously measuring concentrations of analytes in the first fluid sample within at least one formed complex at the interface between the first fluid sample and the composite thin film of the plurality of functionalized detection lanes of the SAW sensor comprises simultaneously measuring concentrations of the analytes in the first fluid sample in the plurality of functionalized detection lanes of the SAW sensor while each of the plurality of functionalized detection lanes is fluid-free.

14. The method of claim 1 where measuring the concentration of the analyte originally suspended in the first fluid sample within the formed complex at the interface between the first fluid sample and the composite thin film of the at least one functionalized detection lane comprises measuring a concentration of the analyte originally suspended in the first fluid sample within the formed complex at the interface between the first fluid sample and the composite thin film of the at least one functionalized detection lane in a calibrated dynamic range of 2 pg/ml to 24 µg/ml.

15. The method of claim 14 where measuring the concentration of the analyte originally suspended in the first fluid sample within the formed complex at the interface between the first fluid sample and the composite thin film of the at least one functionalized detection lane in a calibrated dynamic range of 2 pg/ml to 24 µg/ml comprises measuring a concentration of troponin I within the formed complex at the interface between the first fluid sample and the composite thin film of the at least one functionalized detection lane in a calibrated dynamic range of 2 pg/ml to 24 µg/ml.

16. The method of claim 1 where providing the SAW sensor with at least one functionalized detection lane in a handheld, portable assay device and sensor system comprises providing the SAW sensor in a sensor spin-disk system utilizing a spinning disk cartridge.

17. The method of claim 1 further comprising:
Taking additional multiple fluid samples from the patient at about the same time;
repeating fluidically disposing the multiple fluid samples in the at least one functionalized detection lane, concentrating the analyte suspended in the multiple fluid samples at the surface of the at least one functionalized detection lane to concentrate the multiple samples and increase the probability of forming a specific analyte-antibody complex bound to the at least one functionalized detection lane; and
measuring a concentration of the analyte originally suspended in the multiple fluid samples that is now within the formed complex bound to the at least one functionalized detection lane when a predetermined mass of the analyte has been disposed in the at least one functionalized detection lane.

18. The method of claim 1 further comprising maintaining the at least one functionalized detection lane of the SAW sensor dry until the first fluid sample is fluidically disposed in the at least one detection lane, and
where measuring the concentration of the analyte originally suspended in the first fluid sample within the formed complex at the interface between the first fluid sample and the composite thin film of the at least one functionalized lane comprises measuring the concentration of the analyte originally suspended in the first fluid sample within the formed complex at the interface between the first fluid sample and the composite thin film of the at least one functionalized lane while the at least one functionalized detection lane is fluid-free.

19. The method of claim 1 further comprising washing the at least one functionalized detection lane with a wash fluid to remove any unbound components from the portable assay device and sensor system so that only the specific analyte-antibody complexes bound to the at least one functionalized detection lane remain.

20. The method of claim 19 further comprising flowing a stream of dry gas over the wash fluid to remove it from the at least one functionalized detection lane.

21. The method of claim 1 where increasing the concentration of the analyte in the at least one functionalized detection lane comprises flowing a stream of dry gas over the first fluid sample in the at least one functionalized detection lane to remove any unbound analyte in the first fluid sample and displace it with the dry gas within the at least one functionalized detection lane.

\* \* \* \* \*